United States Patent [19]

Kaste et al.

[11] Patent Number: 4,845,995
[45] Date of Patent: Jul. 11, 1989

[54] MATERIAL TESTER

[75] Inventors: Robert P. Kaste, North East, Md.; Robert E. Tompkins, Oxford, Pa.

[73] Assignee: The United States of America as represented by the Secretary of the Army, Washington, D.C.

[21] Appl. No.: 219,017

[22] Filed: Jul. 14, 1988

[51] Int. Cl.⁴ ............................................. G01N 3/00
[52] U.S. Cl. ...................................... 73/794; 73/825; 73/837; 73/841
[58] Field of Search ................ 73/794, 795, 826, 834, 73/837, 819, 825, 841, 845

[56] References Cited

U.S. PATENT DOCUMENTS

| 2,291,106 | 7/1942 | Ruch | 73/825 |
| 3,563,087 | 2/1971 | Brunelle et al. | 73/825 X |
| 3,610,031 | 10/1971 | Clark et al. | 73/795 |

Primary Examiner—Jerry W. Myracle
Attorney, Agent, or Firm—Saul Elbaum; Thomas E. McDonald; Guy M. Miller

[57] ABSTRACT

A material tester which allows for material characterization under hydrodynamic loading including very high rates of loading such as found in ballistic applications, and which includes various interchangeable fittings to allow the tester to simultaneously subject a test specimen to (1) radial compression and axial tension, or (2) radial compression and axial compression, or (3) radial compression and axial shearing stress.

6 Claims, 4 Drawing Sheets

MATERIAL TESTER

RIGHTS OF THE GOVERNMENT

The invention described herein may be manufactured, used, or licensed by and for the United States Government for governmental purposes without the payment to us of any royalty thereon.

BACKGROUND OF THE INVENTION

1. Technical Field

The invention described herein relates generally to material testing devices, and, in particular, to a material testing device which provides very high rates of axial and radial loadings simultaneously on a specimen being tested.

2. Background Art

The mechanical properties of a material specimen may vary under various combinations of axial and radial loads in tension, compression, and/or shear, depending on the particular type and combination of loads and the rate at which these loads are applied to the material specimen.

The rate of applied loads is usually dealt with by designers on a relatively simplistic basis. It is known that dynamics of loadings affects the stress in a given item and various techniques exist for approximating corrective factors in stress calculations for these differences. For example, the well known Barth equation $\sigma a = \sigma 1200/(1200+v)$, where $\sigma a$ is the design stress of a gear tooth at a pitch velocity v and $\sigma$ is a safe static stress for that tooth, is based on an English rule published in 1869. Likewise, the equation for the shock factor b, $b = (1 + (1 + h/y)\wedge(0.5))$, where h is the height to produce a given velocity of impact and y is the formation produced by a static load of equal magnitude, shows that for an impact, h=0, a factor of 2 is determined to be multiplied to the static load.

These calculations do not include any correction for the response of a given material to dynamic loading. This is partially due to the insensitivity of most material properties to relatively small changes in rates of loading. However, at a very high rate of loading such as that experienced in the field of ballistics a material's response to loading can be quite different from loads of the same magnitude applied at a lower rate or applied for a different duration. Nylon, used in rotating bands for various artillery shells should not work according to the material properties provided by the handbooks, which has data based on static loading. That these bands do work indicates that nylon must behave differently at the high rates of loading in the ballistic application, at least for the duration to which they are subjected to these loads. The properties of nylon have not been documented at these rates of loading.

Also, it is well known that combinations of loads create a so called effective stress which can be quite different from any of the individual applied stresses. Various theories are available to estimate this effective stress for cases with combined loading. Most are conservative which leads to inefficient designing.

Maximum normal stress theory states states that failure occurs when the largest principal stress equals the yield strength, $\sigma = -s_y$.

Maximum shear stress is used for ductile material only and states that yielding occurs in shear loading at a magnitude of half the yield stress in tension.

The Von Mises-Hincky theory evolved from observation that when ductile materials were stress hydrostatically their yield strengths were much higher than their yield strengths in simple tension tests. The theory states that the Von-Mises stress $\sigma$ is related in a quadradic manner to the principal stresses $\sigma_1$, $\sigma_2$, $\sigma = (\sigma_1^2 - \sigma_1\sigma_2 + \sigma_2^2)\wedge(0.5)$.

The ability to characterize material properties for specific combinations of loads at ballistic rates of loading would greatly enhance the designer's ability to generate effective and efficient designs.

There are many material testing devices known to the art. However, none of the known devices for hydrostatically loading test samples provide rates of loading which are required for dynamic characterization. Also, none of the known high rate axial loading devices provide the biaxial and hydrodynamic information required for a complete material characterization.

SUMMARY OF THE INVENTION

Therefore, it is a primary object of the invention to provide a material tester which allows for characterization of material properties under combined biaxial loading at high rates of loading.

It is another object of the invention to provide a material tester which allows for material characterization under hydrodynamic loading including high rates of loading such as found in ballistic applications.

It is a further object of the invention to provide a material tester which allows for material and design test under various biaxial and hydrodynamic loadings at high rates of loading.

It is still another object of the invention to provide a material tester having various interchangeable fittings to allow the tester to simultaneously subject a test specimen to (1) radial compression and axial tension, or (2) radial compression and axial compression, or (3) radial compression and axial shearing stress.

In the invention described herein, a pressure source of controllable magnitude either is created using a propellant charge or is introduced from an external source. This pressure source is released by a burst disk to pressurize a liquid-filled test chamber through one or more connecting orifices which control the rate of pressurization of the liquid. The pressurized liquid creates a radial load on a test sample disposed in the test chamber and forces a piston outward from the test chamber which creates an axial load on the sample. The magnitude of the pressurization and the size of the piston control the axial load on the sample. Both axial and radial loading rates are controlled by the rate of pressurization of the liquid. Various configurations of the connection of the sample to the piston and the body of the device control the direction of the loading on the sample.

BRIEF DESCRIPTION OF THE DRAWINGS

The invention will be better understood, and further objects, features, and advantages thereof will become more apparent from the following description of the preferred embodiment, taken in conjunction with the accompanying drawings in which.

DESCRIPTION OF THE PREFERRED EMBODIMENT

Figure 1:
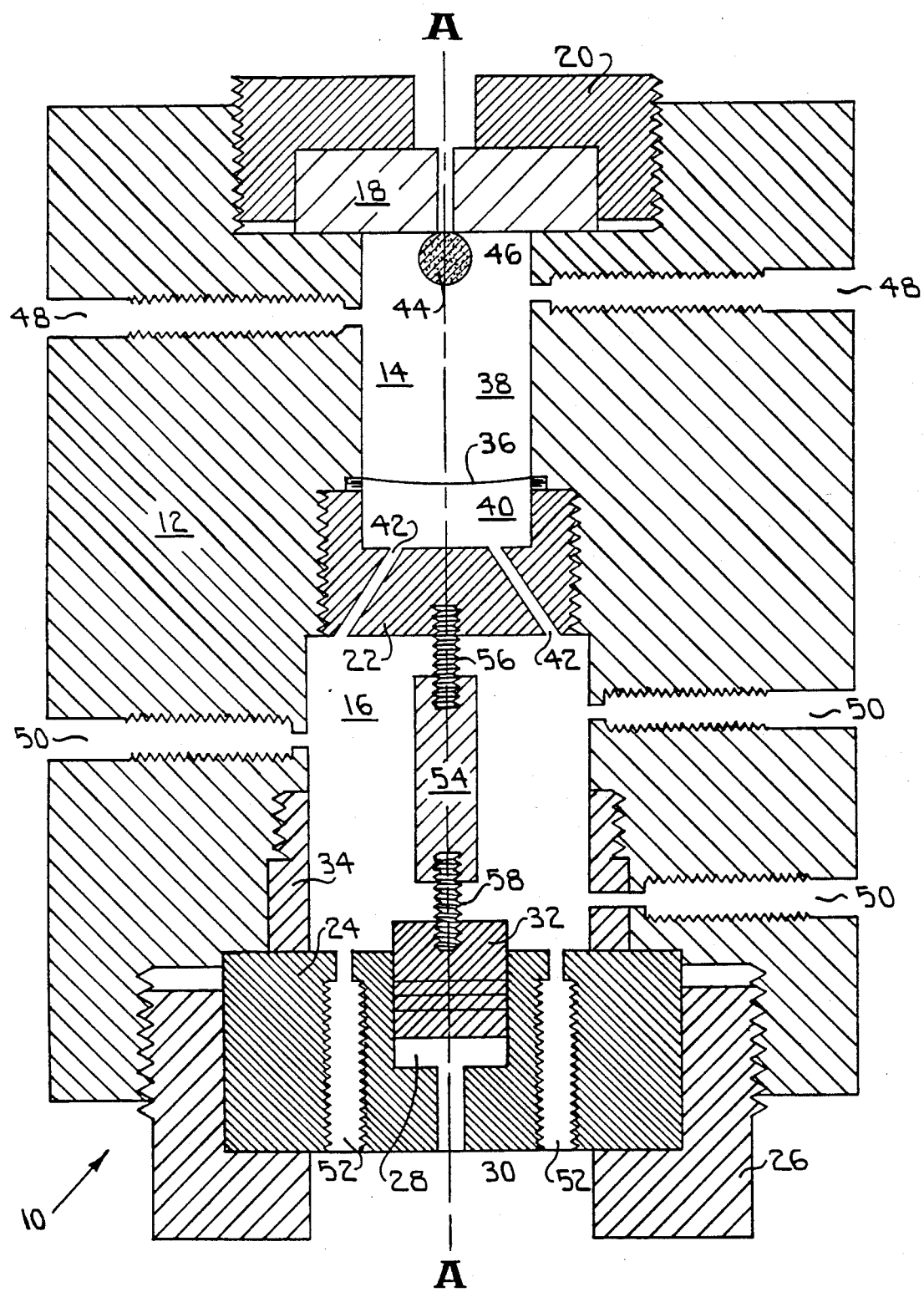
FIG. 1 is a cross sectional side view of the preferred embodiment of the invention, taken along the axis A—A', including a test specimen and fittings for simultaneously subjecting the specimen to radial compression and axial tension.

The material tester 10 shown in FIG. 1 includes a cylindrical body 12 having a center axis A—A'. The body 12 is axially bored and threaded, and various plugs and retainers are secured therein to form a pressure supply chamber 14 and a test chamber 16 capable of testing specimens of various shapes and configurations up to three inches in diameter and ten inches long.

The outer end of the pressure supply chamber 14 is closed by a plug 18 which is positioned and secured to the body 12 by a first threaded retainer 20. The inner end of the pressure supply chamber 14 is closed by a second threaded retainer 22 which also closes the inner end of the test chamber 16. The outer end of the test chamber 16 is closed by a cylinder block 24 which is positioned and secured to the body 12 by a third threaded retainer 26.

The cylinder block 24 includes an axial cylindrical recess 28 having an inner end opening into the test chamber 16 and an outer end which to connected to a low reference pressure (generally ambient air pressure) via a port 30. A piston 32 is slidably disposed within the recess 28 for translation along the axis A—A' in response to the difference between the test chamber pressure and the reference pressure.

Various annular inserts, such as insert 34, may be inserted within the test chamber 16 to reduce the test chamber volume for tests using a small test specimen, thereby keeping the system's response time to a minimum.

During operation of the material tester 10, very high pressure (200 kpsi or more) can be generated in the pressure supply chamber 14. Therefore, the body 12 and the various inserts, plugs, blocks, and retainers 18–34 defining the pressure supply chamber 14 and the test chamber 16 are formed of high strength materials, e.g., high strength steel, of sufficient thickness to withstand this very high pressure.

The second retainer 22 also secures, within the pressure supply chamber 14, a commercially-obtainable shear disc 36 which divides the pressure supply chamber into an outer sub-chamber 38 and an inner sub-chamber 40. This shear disc 36 is designed to shear or fracture when the pressure within the outer sub-chamber 38 exceeds the pressure within the inner sub-chamber 40 by a predetermined value. In the preferred embodiment of the invention, the shear disc 36 is formed of stainless steel which can be stored for long periods of time under adverse conditions without change in its rated shear pressure. However, the shear disc 36 may be formed of other frangible materials commonly used for this purpose.

The second retainer 22 includes a plurality of orifices 42 which are disposed uniformly about the axis A—A' and which connect the inner sub-chamber 40 with the test chamber 16. The inner sub-chamber 40 is gas-filled (generally, air) whereas the test chamber 16 is filled with a liquid, such as water. For this reason, if the material tester 10 is disposed with the axis A—A' horizontal, the orifices 42 are filled with a low shear strength substance, such as silicone grease, to prevent leakage of liquid from the test chamber 16 through the orifices 42 prior to testing. This orifice sealing procedure may not be necessary when the material tester 10 is disposed so that the axis A—A' is vertical and the pressure supply chamber 14 is above the test chamber 16.

The outer sub-chamber 38 of the pressure supply chamber 14 contains a solid or liquid propellant explosive charge 44 centrally disposed on the plug 18 which is ignited by an ignitor 46 affixed within a center bore of the plug 18. In a preferred embodiment of the invention, a small grain size solid propellant, such as Army propellant M-10, is used as the explosive charge 44 in order to achieve a very rapid rise time of pressure within the outer sub-chamber 38 (5 msec or less).

The predetermined pressure at which the shear disc 36 shatters must be substantially higher than the pressure desired to be applied to a test specimen within the test chamber 16 to allow for head loss due to frictional losses in the orifices 42 and damping of the liquid in the test chamber 16. For example, in order to apply a load of 110 kpsi with a rise of 5 msec or less to a test specimen within the test chamber 16, it may be necessary to use a shear disc 36 which is rated to rupture at 200 kpsi.

The body 12 includes a plurality of ports 48 extending from the outside into the pressure supply chamber 14 and ports 50 extending from the outside into the test chamber 16; the cylinder block 24 also includes a plurality of ports 52 extending from the outside into the test chamber 16. Pressure relief devices, or temperature or pressure transducers, such as the Kistler model 607C pressure transducer, may be mounted in some of these ports 48, 50, 52. Some of the test chamber ports 50, 52 may be used for cable outlets from strain or displacement transducers mounted on the test specimen, or for filling the test chamber 16 with minimum ullage.

Interchangeable specimen holding devices are used in the material tester 10 to permit various size and shape specimens of material to be mounted in the test chamber 16 for axial tension, compression or shear loading tests. FIG. 1 shows a specimen 54 arranged for an axial tension loading test. The specimen 54 is centrally disposed within the test chamber 16 and affixed to the second retainer 22 and the piston 32 by respective inner and outer specimen mounting rods 56, 58 to extend along the axis A—A' therebetween. The inner rod 56 has one end which is threadedly engaged with the second retainer 22 within a threaded axial bore of the second retainer 22, and an opposite end which is threadedly engaged with the test specimen 54 within a threaded axial bore at the inner end of the specimen 54. Similarly, the outer rod 58 has one end which is threadedly engaged with the piston 32 within a threaded axial bore of the piston 32, and an opposite end which is threadedly engaged with the test specimen 54 within a threaded axial bore at the outer end of the specimen 54.

A test on the specimen 54 is initiated by the ignition of the explosive charge 44 by the ignitor 46, which produces a rapid increase of pressure in the outer sub-chamber 38 of the pressure supply chamber 14. At a predetermined pressure, the shear disc 36 bursts, causing a very abrupt increase in pressure in the outer subchamber 40 and pressurizing the liquid in the test chamber 16 via the orifices 42. The rate of pressurization of the liquid within the test chamber 16 is controlled by the orifices 42.

The pressurized liquid in the test chamber 16 exerts a force on the piston 32 to move the piston outward from the test chamber 16 along the axis A—A' within the cylindrical recess 28. The piston 32 pulls on the outer rod 58, transmitting an axial tensile load to the specimen 54 via the inner rod 56 which is anchored to the body 12 by the retainer 22. At the same time, the pressurized liquid within the test chamber 16 transmits a radial compressive load to the specimen 54.

To test a material under various loads and rates at which these loads are applied, different explosive charges 44, and/or different size and shape specimens of the material, together with different size or shape tester components, such as shear disc 36, second retainer 22, cylinder block 24 and piston 32 assembly, and insert 34, may be used.

The maximum pressure within the test chamber 16 depends directly on the explosive charge 44. Thus, by increasing the explosive charge 44, the maximum pressure within the test chamber 16 is increased.

The rate at which the pressure within the test chamber 16 increases depends directly on the pressure at which the shear disc 36 ruptures and the head loss through the orifices 42. Thus, by using a shear disc having a higher shear pressure rating and/or using a second retainer 22 having larger diameter orifices or having a larger number of orifices 42, the rate at which the test chamber 16 is pressurized is increased.

Also, the system response time, i.e., the rate of rise of pressure within the test chamber 16, msy be reduced somewhat by using a different insert 34 to reduce the volume of the test chamber 16.

The axial tensile load and the rate at which it is applied to the specimen 54 depends directly on the cross section area of the piston 32 and indirectly on the cross section area of the specimen 54. Thus, the tensile load and the rate at which it is applied to the specimen 54 can be increased by using a specimen of reduced cross section area and/or using a cylinder block and piston assembly having a piston 32 of increased cross section area.

Figure 2:
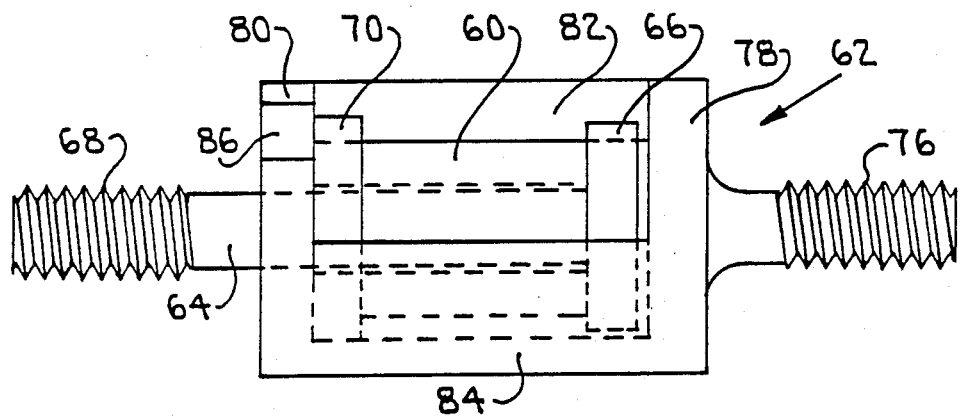
FIG. 2 is a side view of a test specimen and fittings for use in the embodiment of FIG. 1 to a simultaneously subject the specimen to radial and axial compression.
Figure 3:
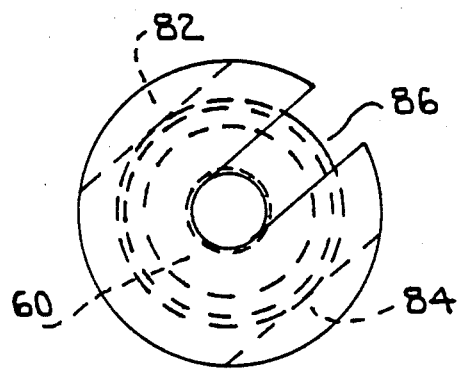
FIG. 3 is an end view of the test specimen and fittings of FIG. 2.

FIGS. 2 and 3 show a material specimen 60 and specimen mounting assembly 62 which can be used in place of the specimen 54 and specimen mounting rods 56, 58 when it is desired to test a material by simultaneously applying axial and radial compressive loads to the material specimen. The specimen mounting assembly includes a rod 64 having an end collar 66 affixed to or integral with one end of the rod 64 and having an opposite threaded end portion 68 which is inserted through the hollow cylindrical test specimen 60 and a circular collar 70, both of which have a larger internal diameter than the rod 64. The threaded end portion 68 is then screwed into the axial threaded bore of the second retainer 22 to affix the rod 64 to the body 12 via the second retainer 22.

The specimen mounting assembly also includes a mounting member 74 which replaces the outer rod 58 of FIG. 1. The mounting member 74 has a threaded end portion 76 which is threadedly engaged with the piston 32 within the threaded axial bore of the piston 32. The mounting member 74 has a circular inner flange 78 and an end flange 80 which is affixed to and spaced from the inner flange 78 by two side members 82, 84 which are spaced apart and are of sufficient length so that the rod 64 carrying the specimen 60 and the collar 70 can be inserted between the inner and end flanges 78, 80 of the mounting member 74. The end flange 80 has a radially extending slot 86 of sufficient width and depth to allow the threaded portion 68 of the rod 64 to be inserted therein so that the rod 64 is coaxial with the mounting member 74.

When the specimen 60 and specimen mounting assembly 62 is used in the material tester 10, the force exerted on the piston 32 by the pressurized liquid within the test chamber 16 causes the piston 32 to pull on the mounting member 74, transmitting an axial compressive load through the collar 70 to the specimen 60, which is prevented from moving by the end collar 66 of the rod 64 affixed to the body 12. At the same time, the pressurized liquid within the test chamber 16 transmits a radial compressive load to the specimen 60.

Figure 4:
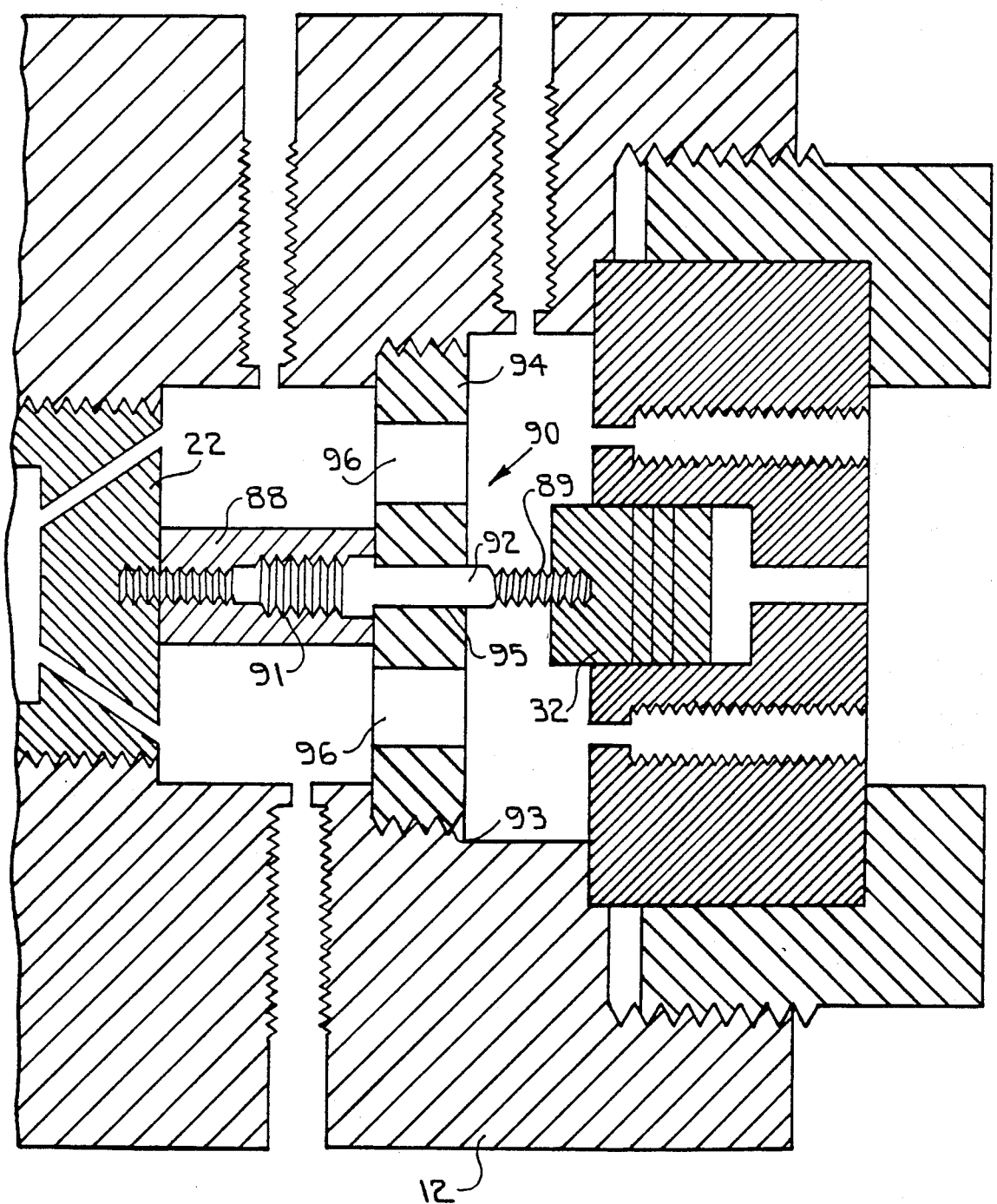
FIG. 4 is a cross section view of part of the embodiment of FIG. 1, showing a test sample and fittings for simultaneously subjecting the specimen to radial compression and axial shearing stress.

FIG. 4 shows a cylindrical material specimen 88 and specimen mounting assembly 90 which can be used in place of the specimen 54 and specimen mounting rods 56, 58 when it is desired to test a material by simultaneously applying a radial compressive load and an axial shear load to the material specimen. The specimen mounting assembly 90 includes: (1) an axial-extending rod 92 having one end 89 which is threadedly engaged with the piston 32 and having an opposite end 91 which is threadedly engaged with the specimen 88; and (2) a disc-shaped support member 94 having a threaded periphery 93 which is threadedly engaged with the body 12 to hold the specimen 88 tightly against the second retainer 22, a center bore 95 through which the rod 92 freely extends, and a plurality of openings 96 to allow the rapid pressurization of liquid adjacent the piston 32.

During operation of the material tester 10, the force exerted on the piston 32 by the pressurized liquid within test chamber 16 causes the piston 32 to pull on the rod 92, which in turn applies an axial shear load to the specimen 88, which is prevented from moving by the support member 94. At the same time, the pressurized liquid within the test chamber 16 transmits a radial compressive load to the specimen 88.

Figure 5:
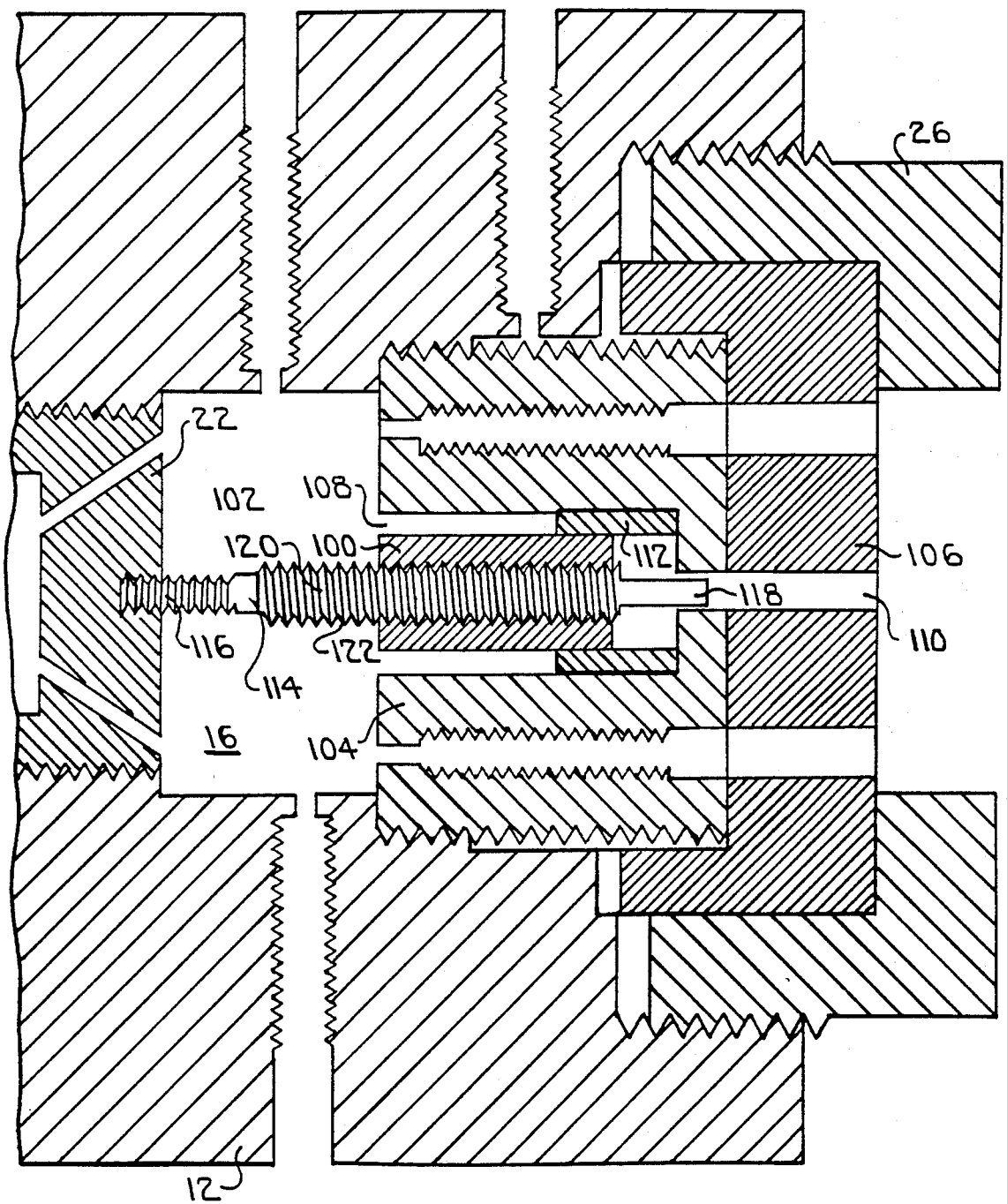
FIG. 5 is a cross section view of part of the embodiment of FIG. 1, showing another test sample and fittings for simultaneously subjecting the specimen to radial compression and axial shearing stress.

FIG. 5 shows a material specimen 100 and alternate specimen mounting arrangement 102 which can be used in the material tester 10 when it is desired to test a material by simultaneously applying a radial compressive load and an axial shear load to the material specimen. In this arrangement, the cylinder block 24 of FIG. 1 is replaced by a cylinder block 104 and an adapter plug 106 disposed between the cylinder block 104 and the third threaded retainer 26. The cylinder block 104 has a threaded periphery which is engaged with the threaded portion of the test chamber side wall, to thus minimize the test chamber volume. The cylinder block 104 includes an axial cylindrical bore 108 opening into the test chamber 16 and connected to an ambient or low pressure reference by an axial port 110 extending through the adapter plug 106. In addition, the cylinder block 104 includes a sleave 112 disposed in the bottom portion of the bore 108.

This arrangement 102 also includes an axially-extending rod 114 affixed to the body 12 via the second retainer 22. The rod 114 has a threaded end portion 116 which is tightly screwed into the threaded center bore of the second retainer 22, an opposite end portion 118 extending concentrically within the port 110, and an intermediate portion 120 having a plurality of radially-extending flanges or collars 122.

The cylindrical material specimen 100 is disposed about the intermediate portion 120 of the rod 114 and extends into the sleeve 112. The specimen 100 has a center bore surface which conforms in shape to the surface of the intermediate portion 120 of the rod 114 in close contact therewith, and has an outer surface in slidable contact with the sleeve 112. The specimen 100 can be molded or cast about the rod 114, or can be formed as two or three identical radial segments extending axially the length of the specimen 100. The specimen 100 serves as the piston of the cylinder block 104.

During operation of the tester 10, the pressurized liquid within the test chamber 16 applies an axial shear load and simultaneously applies a radial compressive load to the specimen 100.

The various threaded connections of the device parts are shown only as a concept, and other techniques such as clamping for assembly can be used. For example, in the embodiment of FIG. 1, the second retainer 22 and the piston 32 may be provided with spade type connectors and the specimen 54 likewise provided with similar spade connectors which are bolted to the respective piston and second retainer spade connectors.

Since there are many variations, additions and changes to the embodiments described herein which would be obvious to one skilled in the art, it is intended that the scope of the invention be only limited by the appended claims.

What is claimed and desired to be secured by Letters Patent of the United States is:

1. A material tester, having an axis, for simultaneously applying an axial load and a radial load to a test sample, said tester comprising:

a fluid-filled first chamber extending along said axis between a first end wall and a second end wall, the first end wall of the first chamber including a first passageway extending therethrough between an inner end and an outer end, at least the inner end of said first passageway being formed as a first cylindrical passage extending concentrically about and along said axis, said first passageway being closed by a piston slidably disposed within the first cylindrical passage for limited movement therein along said axis in response to a difference between pressure within the first chamber acting on an inner end of the piston and pressure at the outer end of the first passageway acting on an outer end of the piston;

first chamber access means for opening the first chamber to permit the test sample to be mounted therein;

test sample mounting means for mounting the test sample within the first chamber so that the test sample extends symmetrically along said axis, one portion of the test sample being affixed to the piston and another portion of the test sample being affixed to the second end wall of the first chamber; and pressure supply means for pressurizing the fluid within the first chamber, said pressurized fluid acting on the inner end of the piston to cause the piston to exert an axial load on the test sample, and said pressurized fluid directly exerting a radial load on the test sample, wherein the pressure supply means comprises a second chamber, having a frangible shear disc mounted therein which divides the second chamber into first and second fluid-filled sub-chambers, said shear disc rupturing when the pressure in the second sub-chamber increases to a predetermined value above the pressure in the first sub-chamber, orifice means for maintaining the first sub-chamber in communication with the first chamber, and pressure generating means for increasing the fluid pressure within the second sub-chamber until the shear disc ruptures, producing a rapid rise in pressure within the first chamber.

2. A material tester, as described in claim 1, wherein the pressure generating means comprises: an explosive charge disposed within the second sub-chamber; and ignitor means for actuating the explosive charge.

3. A material tester, as described in claim 1, wherein the first chamber is filled with a liquid.

4. A material tester, as described in claim 1, wherein the test sample mounting means comprises a set of fittings for applying axial loads to the test sample in tension.

5. A material tester, as described in claim 1, wherein the test sample mounting means comprises a set of fittings for applying axial loads to the test sample in compression.

6. A material tester, as described in claim 1, wherein the test sample mounting means comprises a set of fittings for applying axial loads to the test sample in shear.

* * * * *